United States Patent

Visser et al.

[11] Patent Number: 5,952,140
[45] Date of Patent: Sep. 14, 1999

[54] BIPOLAR CHARGE TRANSPORT MATERIALS USEFUL IN ELECTROPHOTOGRAPHY

[75] Inventors: Susan A. Visser, Rochester; Paul M. Borsenberger, Hilton; Jeanne E. Kaeding; Bruce J. Murray, both of Rochester, all of N.Y.

[73] Assignee: Eastman Kodak Company, Rochester, N.Y.

[21] Appl. No.: 09/070,377

[22] Filed: Apr. 30, 1998

[51] Int. Cl.$^6$ .................. G03G 5/047; C07D 471/00
[52] U.S. Cl. .................................... 430/59; 546/70
[58] Field of Search ............... 430/56, 59; 546/70, 546/37

[56] References Cited

U.S. PATENT DOCUMENTS

| | | | |
|---|---|---|---|
| 5,028,504 | 7/1991 | Rule et al. | 430/59 |
| 5,059,503 | 10/1991 | Muto et al. | 430/59 |
| 5,077,161 | 12/1991 | Law | 430/59 |

OTHER PUBLICATIONS

B.J. Murray, J.E. Kaeding, W.T. Gruenbaum, and P.M. Borsenberger, *Jpn. Appl. Phys.* 1996, 35, 5384–5388.
J.E. Kaeding, B.J. Murray, W.T. Gruenbaum, and P.M. Brosenberger, *J. Imag. Sci. Technol.* 1996, 40, 245–248.
W. Sorenson and T. Campbell, *Preparative Methods of Polymer Chemistry*, p. 137, Interscience (1968).

*Primary Examiner*—John Goodrow
*Attorney, Agent, or Firm*—Doreen M. Wells

[57] ABSTRACT

A bipolar charge transport material that is useful in electrophotography, said bipolar charge transport material N,N'-bis-[p-(di-p-tolylamino)phenyl]-1,4,5,8-naphthalenetetracarboxylic acid having the structure:

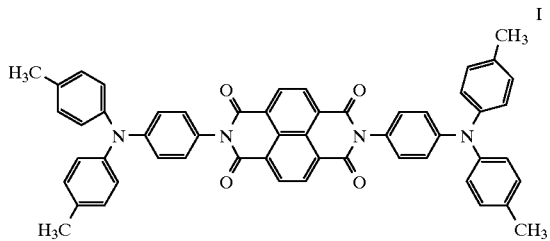

15 Claims, No Drawings

BIPOLAR CHARGE TRANSPORT MATERIALS USEFUL IN ELECTROPHOTOGRAPHY

CROSS REFERENCE TO RELATED APPLICATIONS

This application is related to the following commonly owned US application filed on even date herewith: U.S. Ser. No. 09/070,705 of Visser, Borsenberger and Kaeding, titled "BIPOLAR ELECTROPHOTO-GRAPHIC ELEMENTS". The contents of that related application are incorporated herein in their entirety.

FIELD OF THE INVENTION

This invention relates to electrophotographic materials and electrophotographic elements. In particular, it relates to bipolar charge transport materials useful in electrophotography and to photoconductive elements containing bipolar charge transport materials.

BACKGROUND OF THE INVENTION

Electrophotographic imaging processes and techniques have been extensively described in patents and other literature. The initial image forming step in the electrophotographic process cycle is the creation of an electrostatic latent image on the surface of a photoconductive element. This can be accomplished by charging the photoconductive element in the dark, such as through use of a corona or biased roller charging element. An electrostatic latent image is then formed by image-wise exposing the photoconductive element either optically or by electronic means, such as a laser or an array of light-emitting diodes. The image exposure creates free electron-hole pairs which migrate through the photoconductive element under the influence of the electric field. In such a manner, the surface charge is dissipated in the exposed regions, thus creating an electrostatic charge pattern. A visible image is then formed by depositing electrophotographic toner, comprised of electrically charged marking particles, onto the electrostatic latent image during a development step.

Two methods of development are used in electrophotography: discharged area development (DAD) and charged area development (CAD). The former uses toner of the same polarity as the surface charge on the photoconductive element. The latter utilizes toner of polarity opposite to the polarity of the charge on the element. CAD is widely used in optical copiers, while DAD is more frequently used for digital applications.

The image formed in the development step is transferred to a suitable receiver, such as transparency stock or paper. It can be transferred to a receiver directly, with the assistance of, for example, an electric field or through the application of heat, pressure, or heat and pressure. Alternatively, the image can be first transferred to an intermediate member and, subsequently, transferred to the receiver. Color images can be made by transferring images comprised of the primary colors, (i.e., cyan, magenta, yellow, and black) in register, to either the receiver or the intermediate member.

After transfer, the image is permanently fused to the receiver via a suitable fusing process. In preparation for the next electrophotographic cycle, the photoconductive element is typically cleaned of residual toner because the transfer step is not 100% efficient. Cleaning efficiency is increased by electrostatically conditioning the photoconductive element and residual toner with a charging element known as a pre-clean charger. Cleaning by any of a number of methods known to one skilled in the art is then performed.

Photoconductive elements, also called photoreceptors, are composed of an electrically conductive support and at least one active layer which is insulating in the dark but which becomes conductive upon exposure to light. The support may be in one of many forms, for example, a drum, a web or belt, or a plate. The photoreceptor can comprise one or multiple active layers. The active layer(s) typically contains one or more materials capable of the photogeneration of charge carriers (electrons or holes) and one or more materials capable of transport of the generated charge carriers.

Numerous materials have been described as being useful components of the photoconductive element. These include inorganic substances, such as selenium and zinc oxide, and organic compounds, both monomeric and polymeric, such as arylamines, arylmethanes, carbazoles, pyrroles, phthalocyanines, dye-polymer aggregates, and the like. Organic compounds are particularly useful for several reasons. They can be prepared as flexible layers; as such, the copier or printer architecture is not limited to a particular configuration. Organic compounds have spectral sensitivities that can extend throughout the visible and into the near infrared regions of the spectrum. Organic compounds are amenable to low cost large area manufacturing processes. Elements prepared from organic materials are known as organic photoconductors (OPCs).

OPCs can be prepared with single or multiple active layers. In most OPCs, charge transport occurs through movement of a single type of charge carrier, electrons or holes, but not both. When only one carrier is mobile, trapped carriers of opposite sign can be created, resulting in a change in sensitometry of the active layer with succive cycles, a phenomenon known as latent image hysteresis. One solution to the problem of latent image hysteresis is to separate the charge generation and transport functions into separate layers, referred to as the charge generation (CGL) and charge transport (CTL) layers, to form a dual or multi-layer photoconductive element. These elements offer additional advantages of improved process lifetimes that make them useful in high volume copying and printing applications. A disadvantage of the multiple layer architecture is that only one polarity of surface potential may be employed, limiting the electrophotographic processes in which the element can be used.

Few bipolar charge transport materials (CTMs) capable of transporting both carrier types are known. The known materials have several disadvantages. They are composed of complexes of at least two separate molecules. The necessity to form the complexes increases both the complexity of the manufacture of photoconductive elements and the likelihood that imperfectly formed complexes will give rise to defect points or nonuniformities in a photoconductive layer of the elements. Also, the complexes are not stable over long periods of time. Thus, there is a need for a bipolar CTM that is a single material, a molecular bipolar CTM, that is useful in photoconductive elements used in electrophotography.

Only one molecular bipolar charge transport material capable of transporting both electrons and holes is known. Murray et al. (B. J. Murray, J. E. Kaeding, W. T. Gruenbaum, and P. M. Borsenberger, *Jpn. J. Appl. Phys.* 1996, 35, 5384–5388) reported that N-(p-(di-p-tolylamino)phenyl)-N'-(1,2-dimethylpropyl)-1,4,5,8-naphthalenetetracarboxylic diimide (TAND), in combination with an amorphous selenium CGL, could transport both electrons and holes. Amorphous selenium is undesirable for practical application in a photoconductive element because of the hazards associated with its deposition and disposal. Further, its spectral sensitivity extends to only 500 nm, too low for applications using laser or LED exposure. Kaeding et al. (J. E. Kaeding, B. J. Murray, W. T. Gruenbaum, and P. M. Borsenberger, *J. Imag. Sci. Technol.* 1996, 40, 245–248) further reported bipolar transport by TAND in combination with an unspecified perylene diimide. While the electron and hole mobilities of TAND are analyzed in this paper, no mention is made of the electrophotographic properties of a photoconductive element containing TAND in combination with a CGL that would be useful in an electrophotographic process. The information in these papers is insufficient to determine the usefulness of TAND as a bipolar CTM in a photoconductive element for use in an electrophotographic process.

The electrophotographic properties that a useful bipolar CTM must impart to a photoconductive element are high sensitivity and low residual voltage. The sensitivity is characterized by the exposure energy ($E_{50\%}$), the energy required to discharge the photoconductive element from an initial potential to a final potential that is half the initial potential, for example from an initial potential of 350 V to a final potential of 175 V. Higher exposure energies indicate a less sensitive photoconductive element, one in which higher energy exposures would be required to generate the latent image. The residual voltage ($V_r$) is a measure of the charge remaining on the element after exposing the element and allowing the surface potential to discharge. High residual voltages can give rise to lower potential differences between charged and discharged areas of the element on subsequent imaging cycles. Blurred, fogged, or incomplete images can result. For high process efficiency, low exposure energies and low residual voltages are desired.

A useful bipolar CTM must be capable of producing a photoconductive element that displays the desirable electrophotographic properties under both polarities of initial surface charge. A useful bipolar CTM can be defined as one in which, when incorporated into a photoconductive element, results in a specific ratio of the exposure energies of the element measured under positive and negative polarity initial charging. Specifically, if the exposure energy of the element after positive polarity charging is denoted $E^+_{50\%}$ and if the exposure energy of the element after negative polarity charging is denoted $E^-_{50\%}$, then a bipolar CTM is one which produces a photoconductive element having $\alpha = E^+_{50\%}/E^-_{50\%}$, where $\alpha$ is between 0.25 and 4.0. Both $E^+_{50\%}$ and $E^-_{50\%}$ are measured in erg/cm$^2$ and measure the energy necessary to discharge the photoconductive element from an initial voltage (e.g., 350 V) to half the initial voltage (e.g., 175 V).

SUMMARY OF THE INVENTION

It is an object of the present invention to provide a bipolar charge transport material that is useful in electrophotography, said bipolar charge transport material N,N'-bis-[p-(di-p-tolylamino)phenyl]-1,4,5,8-naphthalenetetracarboxylic acid having the structure:

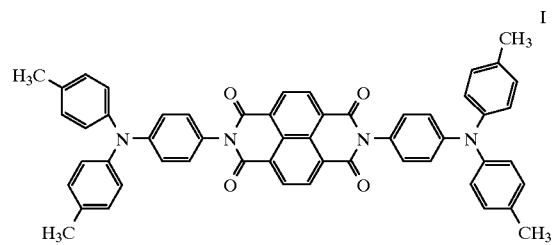

It is a further object of the invention to provide photoconductive elements comprising an electrically conductive base and at least one active layer, said active layer comprising N,N'-bis-[p-(di-p-tolylamino)phenyl]-1,4,5,8-naphthalenetetracarboxylic acid and at least one perylene charge generation material of the structure II:

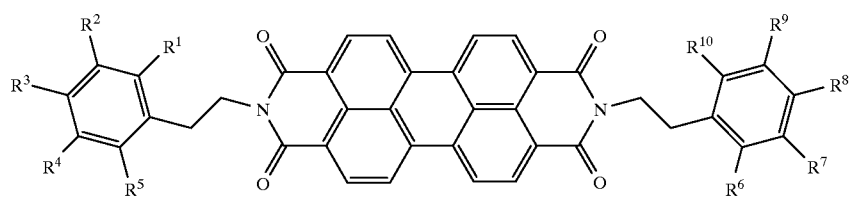

wherein $R^1$, $R^2$, $R^3$, $R^4$, $R^5$, $R^6$, $R^7$, $R^8$, $R^9$, and $R^{10}$ are, each independently, H, CH$_3$, or C$_2$–C$_4$ alkyl, linear or branched. It is preferred that at least two of $R^1$, $R^2$, $R^3$, $R^4$, and $R^5$ are H and that at least two of $R^6$, $R^7$, $R^8$, $R^9$, and $R^{10}$ are H. More preferred structures are those in which at least three of $R^1$, $R^2$, $R^3$, $R^4$, and $R^5$ are H and at least three of $R^6$, $R^7$, $R^8$, $R^9$, and $R^{10}$ are H. Still more preferred those structures II are those in which either all of $R^1$, $R^2$, $R^3$, $R^4$, $R^5$, $R^6$, $R^8$, $R^9$, and $R^{10}$ are H, and $R^7$ is CH$_3$; or all of $R^1$, $R^3$, $R^4$, $R^5$, $R^6$, $R^8$, $R^9$, and $R^{10}$ are H, and both $R^2$ and $R^7$ are CH$_3$;.

Most preferred is that structure II in which all of $R^1$, $R^2$, $R^3$, $R^4$, $R^5$, $R^6$, $R^7$, $R^8$, $R^9$, and $R^{10}$ are H.

It is still a further object of the invention to provide photoconductive elements comprising the bipolar charge transport material of structure I and perylene charge generation materials of the structure III:

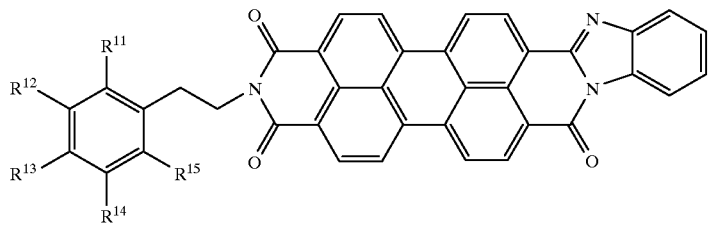

wherein $R^{11}$, $R^{12}$, $R^{13}$, $R^{14}$, and $R^{15}$ being, each independently, H, $CH_3$, or $C_2$–$C_4$ alkyl, linear or branched. It is preferred that $R^{11}$, $R^{13}$, $R^{14}$, and $R^{15}$ are H and $R^{12}$ is H or $CH_3$.

DETAILED DESCRIPTION OF THE INVENTION

This invention deals with bipolar charge transport materials of structure I that are useful in electrophotography:

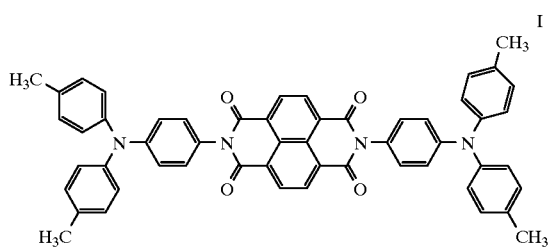

The bipolar charge transport material of structure I, N,N-bis(p-(di-p-tolylamino) phenyl)-1,4,5,8-naphthalenetetracarboxylic acid (BIND), is useful as a bipolar CTM in photoconductive elements used in electrophotographic apparatus, such as copiers or printers. Photoconductive elements containing BIND are particularly useful in those processes in which both negative and positive polarity charging of the element are used, either in the same process cycle or in different process cycles, to achieve advantageous results.

The bipolar CTM of this invention is useful in preparing a photoconductive element when combined with a useful charge generation material (CGM). The choice of CGM to be used in combination with BIND depends on the relative oxidation or reduction potentials of the CGM and CTM. The oxidation potential is the relevant value in the case of hole transport; the reduction potential is the relevant parameter for electron transport. It is only when an appropriate match of potentials between the CGM and CTM is achieved that a useful photoconductive element can be prepared. In practice, this requires that both the oxidation and reduction potentials of the CTM be lower than the CGM.

BIND and an appropriately matched CGM may be present in a single photoconductive layer or in two or more layers that perform the functions of charge generation and transport. The single or multiple layers are known as the active layers. The layer structure may be of the function separated type, in which the charge transport and charge generation functions are in separate layers, or of the single layer type, in which both charge generation and charge transport occur in the same layer.

The synthesis of BIND can be accomplished as described in Example 1.

In addition to BIND and the specified charge generation materials, the active layers may contain one or more binder materials. The binder should provide little or no interference with the generation and transport of charges in the layer. The binder can also be selected to provide additional functions, such as improving adhesion to another layer or providing a smooth, easily cleaned, wear-resistant surface in a top layer. Common binder types include styrene-butadiene copolymers; vinyl toluene-styrene copolymers; styrene-alkyd resins; silicone-alkyd resins; soya-alkyd resins; vinylidene chloride-vinylchloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; poly (methylstyrene); polystyrene; isobutylene polymers; polyesters, such as poly{ethylene-co-alkylene bis (alkyleneoxyaryl) phenylenedicarboxylate}; phenol-formaldehyde resins; ketone resins; polyamides; polycarbonates; polythiocarbonates; copolymers of vinyl haloacrylates and vinyl acetate such as poly(vinyl-m-bromobenzoate-co-vinyl acetate); chlorinated poly(olefins), such as chlorinated poly(ethylene); cellulose derivatives such as cellulose acetate, cellulose acetate butyrate, and ethyl cellulose; and polyimides such as poly{1,1,3-trimethyl-3-(4'-phenyl)-5-indane pyromellitirnide}. One group of polyester binders useful in a charge transport layer is the subject of commonly assigned, co-pending U.S. Ser. No. 08/584,502, entitled ELECTROPHOTOGRAPHIC ELEMENTS HAVING CHARGE TRANSPORT LAYERS CONTAINING HIGH MOBILITY POLYESTER BINDERS of Sorriero, O'Regan and Borsenberger, filed on Jan. 11, 1996. The polyester binders have the following structural formula:

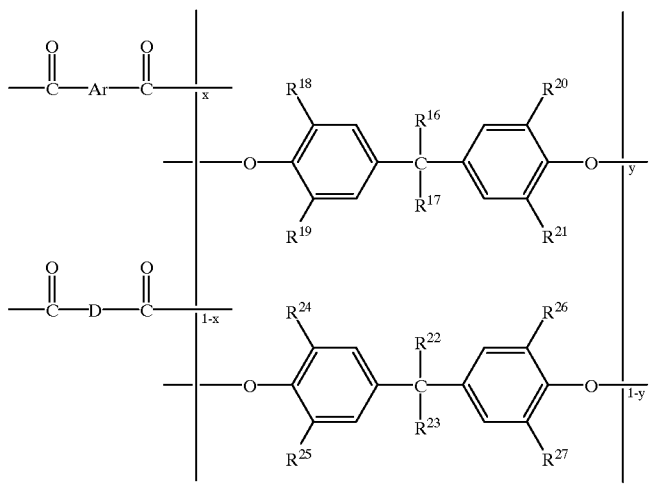

wherein:

Ar represents phenylene, terephthaloyl, isophthaloyl, 5-t-butyl-1,3-phenylene or phenylene indane;

D represents alkylene, linear or branched, or cycloalkylene, having from 4 to about 12 carbons;

$R^{16}$, $R^{17}$, $R^{22}$, and $R^{23}$ represent H, alkyl having 1 to 4 carbon atoms, cyclohexyl, norbornyl, phenylindanyl, perfluoralkyl having 1 to 4 carbon atoms, α, α-dihydrofluoroalkyl having 1 to 4 carbon atoms, or α, α, ω-hydrofluoroalkyl having 1 to 4 carbon atoms; and $R^{18}$, $R^{19}$, $R^{20}$, $R^{21}$, $R^{24}$, $R^{25}$, $R^{25}$, and $R^{27}$ represent H, halogen, or alkyl having from 1 to about 6 carbons; x is from 0 to 0.8; and y is from 0 to 1, with x and y being mole ratios.

The polyester binders can be prepared using well known solution polymerization techniques such as disclosed in W. Sorenson and T. Campbell, Preparative Methods of Polymer Chemistry, page 137, Interscience (1968). Schotten-Baumann conditions were employed to prepare the following examples of useful polyester binders: poly{4,4'-isopropylidene bisphenylene terephthalate-co-azelate (70/30)}; poly{4,4'-isopropylidene bisphenylene terephthalate-co-isophthalate-co-azelate (50/25/25)}; poly{4,4'-isopropylidene bisphenylene-co-4,4'-hexafluoroisopropylidene bisphenylene (75/25) terephthalate-co-azelate (65/35)}; poly{4,4'-isopropylidene bisphenylene-co-4,4'-hexafluroisopropylidene bisphenylene (50/50) terephthalate-co-azelate (65/35)}; poly{4,4'-hexafluoroisopropylidene bisphenylene terephthalate-co-azelate (65/35)}; poly{hexafluoroisopropylidene bisphenylene terephthalate-co-isophthalate-co-azelate (50/25/25)}; and poly{4,4'-isopropylidene bisphenylene isophthalate-co-azelate (50/50)}.

Examples of binder polymers which are particularly desirable from the viewpoint of minimizing interference with the generation or transport of charges include: bisphenol-A polycarbonates and polyesters such as poly[(4,4'-norbornylidene)diphenylene terephthalate-co-azelate]. Polyester ionomers are useful as well. Examples of such polyester ionomers include:

poly[1,4-cyclohexylenedimethylene-co-2,2'-oxydiethylene (46/54) isophthalate-co-5-sodiosulfoisophthalate (95/5)];

poly[1,4-cyclohexylenedimethylene-co-2,2'-oxydiethylene (46/54) isophthalate-co-5-sodiosulfoisophthalate (90/10)];

poly[1,4-cyclohexylenedimethylene-co-2,2'-oxydiethylene (46/54) isophthalate-co-5-sodiosulfoisophthalate (85/15)];

poly[1,4-cyclohexylenedimethylene-co-2,2'-oxydiethylene (46/54) isophthalate-co-5-sodiosulfoisophthalate (80/20)];

poly[1,4-cyclohexylenedimethylene-co-2,2'-oxydiethylene (46/54) isophthalate-co-5-sodiosulfoisophthalate (75/25)];

poly[1,4-cyclohexylenedimethylene-co-2,2'-oxydiethylene (46/54) isophthalate-co-5-lithiosulfoisophthalate (90/10)];

poly[1,4-cyclohexylenedimethylene-co-2,2'-oxydiethylene (46/54) isophthalate-co-triphenylmethylphosphoniumsulfoisophthalate (90/10)];

poly[1,4-cyclohexylenedimethylene-co-2,2'-oxydiethylene (46/54) isophthalate-co-5-(4-sulfophenoxy)isophthalate (90/10)];

poly[1,4-cyclohexyloxydiethylene terephthalate-co-4-(4-sulfophenoxy)isophthalate (70/30)]; and poly(1,4-cyclohexylenedimethylene-co-2,2'-oxydiethylene (46/54) isophthalate-co-4,4'-dicarboxyphenylmethylphenyl phosphonium p-toluenesulfonate (90/10)].

When a polymeric binder is employed in either the CGL or CTL, the optimum ratio of CGM or CTM to binder may vary widely depending on the particular binder and CGMs or CTMs. In general, useful results are obtained when the amount of active CGM or CTM contained within the layer varies within the range of from about 2 to about 90 weight percent based on the dry weight of the layer.

The active layers of the elements of this invention can contain more than one of the CGMs of this invention in combination with BIND. Further, a single active layer or a CGL containing one or more of the CGMs of this invention can also be combined with appropriate spectral sensitizing dyes or chemical sensitizers in order to control the sensitivity of the layer to particular wavelengths of radiation. For photoconductive elements of the function separated, multilayer type, it is also possible to include a CTM in a CGL, as is known to one skilled in the art. Examples of CTMs known to be useful in CGLs include arylamines, particularly triarylamines, and polyarylalkanes, in particular 1,1-bis(di-4-tolylaminophenyl)-cyclohexane) and 4N,N-(diethylamino)tetraphenylmethane. For elements containing more than one CGL, there may be different CTMs in each CGL. The CTMs used in the CGL need not be BIND, the primary charge transport material in the CTL.

For a bipolar photoconductive element of the function separated type, the thickness of the CTL may vary. A preferred thickness for the CTL is from about 2 to about 50 micrometers ($\mu$m) dry thickness. A more preferred range is from about 5 to about 20 $\mu$m. The CTL in a function-separated type photoconductive element can be a single layer or multiple layers.

For a bipolar photoconductive element of the single layer type, the thickness of the active layer may vary. A preferred thickness for the layer is from about 2 to about 50 $\mu$m. A more preferred range is from about 5 to about 20 $\mu$m.

The precise concentration of BIND in the bipolar photoconductive elements of this invention can be varied to achieve optimal function, as is known to those skilled in the art. A preferred concentration of BIND is from 2–100 weight percent (wt %), based on the dry weight of the active layer containing the BIND. A more preferred concentration is 30–100 wt %. Those skilled in the art will understand that the optimal concentration of BIND will differ depending on whether the bipolar photoconductive element is of the single layer or function separated type, with the highest BIND concentration (e.g., 100 wt %) being useful primarily in the function-separated elements.

Coating aids, such as levelers, surfactants, crosslinking agents, colorants, plasticizers, and the like can be added to the layers of this invention. The quantity of each of the respective additives present in a coating composition can vary, depending upon the results desired and user preferences. The layers can also optionally contain other addenda such as sensitizers (spectral sensitizing dyes and chemical sensitizers), contrast control agents, and release agents, as is well known in the art.

Numerous materials are known to be useful as CGMs, including dye-polymer aggregates, phthalocyanines, squaraines, perylenes, azo-compounds and trigonal selenium particles. Preferred CGMs useful in combination with BIND in the photoconductive elements of this invention is represented by structures II:

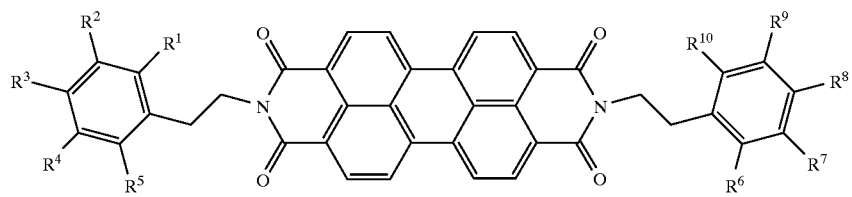

II wherein $R^1$, $R^2$, $R^3$, $R^4$, $R^5$, $R^6$, $R^7$, $R^8$, $R^9$, and $R^{10}$ are, each independently, H, $CH_3$, or $C_2$–$C_4$ alkyl, linear or branched. It is preferred that at least two of $R^1$, $R^2$, $R^3$, $R^4$, and $R^5$ are H and that at least two of $R^6$, $R^7$, $R^8$, $R^9$, and $R^{10}$ are H. More preferred structures are those in which at least three of $R^1$, $R^2$, $R^3$, $R^4$, and $R^5$ are H and at least three of $R^6$, $R^7$, $R^8$, $R^9$, and $R^{10}$ are H. Still more preferred are those structures II in which either all of $R^1$, $R^2$, $R^3$, $R^4$, $R^5$, $R^6$, $R^8$, $R^9$, and $R^{10}$ are H, and $R^7$ is $CH_3$; or all of $R^1$, $R^3$, $R^4$, $R^5$, $R^6$, $R^8$, $R^9$, and $R^{10}$ are H, and both $R^2$ and $R^7$ are $CH_3$;.

Most preferred is that structure II in which all of $R^1$, $R^2$, $R^3$, $R^4$, $R^5$, $R^6$, $R^7$, $R^8$, $R^9$, and $R^{10}$ are H.

Also preferred as CGMs to be used in combination with BIND to produce photoconductive elements of the invention are materials of the structure III:

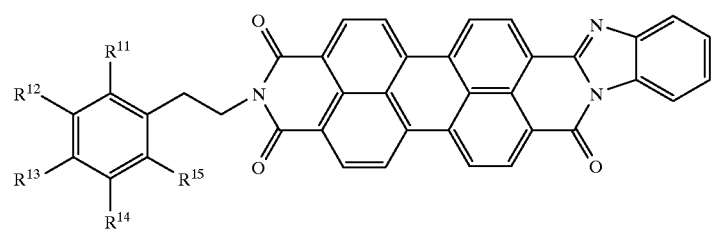

III wherein $R^{11}$, $R^{12}$, $R^{13}$, $R^{14}$, and $R^{15}$ being, each independently, H, $CH_3$, or $C_2$–$C_4$ alkyl, linear or branched. It is preferred that $R^{11}$, $R^{13}$, $R^{14}$, and $R^{15}$ are H and $R^{12}$ is H or $CH_3$.

When prepared as part of a CGL, the CGMs of structures II and III can be prepared as dispersions in a polymeric binder or as vacuum-evaporated pure materials. Additional CGMs and various sensitizing materials, such as spectral sensitizing dyes and chemical sensitizers may also be incorporated in a CGL.

A useful thickness for a CGL is within the range of from about 0.1 to about 10 $\mu$m dry thickness, particularly from about 0.5 to about 5 $\mu$m.

In one method of preparation of the active layers of the elements of the invention, the components of the layer, including binder and any desired addenda, are dissolved or dispersed together in an organic solvent to form a coating composition which is then solvent coated over a conductive support. The liquid is then caused to evaporate from the mixture to form the active layer.

Suitable organic solvents include aromatic hydrocarbons such as benzene, toluene, xylene and mesitylene; ketones such as acetone, butanone and 4-methyl-2-pentanone; halogenated hydrocarbons such as dichloromethane, 1,1,2-trichloroethane, chloroform and ethylene chloride; ethers including ethyl ether and cyclic ethers such as dioxane and tetrahydrofuran; other solvents such as acetonitrile and dimethylsulfoxide; and mixtures of such solvents. The amount of solvent used in forming the binder solution is typically in the range of from about 2 to about 100 parts of solvent per part of binder by weight, and preferably in the range of from about 10 to 50 parts of solvent per part of binder by weight.

Another method for deposition of one or more of the active layers of the elements of this invention is vacuum evaporation. In multilayer photoconductive elements, it is possible to deposit only one of the layers by vacuum evaporation and the rest by coating from a solution or to deposit some fraction of the layers by vacuum evaporation and the rest by coating from a solution.

A substrate can be either flexible or rigid for use in, for example, either web or drum format. A flexible substrate can be either electrically insulating or conducting. Suitable materials include polymers such as poly(ethylene terphthalate), nylon, polycarbonate, poly(vinyl butyral), poly(ethylene), etc., as well as aluminum, stainless steel, ceramics, ceramers, etc. If the substrate material is electrically insulating, it should be coated by a suitable process such as evaporation, sputtering, painting, solvent coating, etc., with a conductive layer such as nickel, copper, gold, aluminum, chromium, or suitable conducting polymers. An electrically conductive substrate material alone or the combination of an insulating substrate and an electrically conductive layer shall be referred to herein as an electrically conductive base.

The active layers of the photoconductive elements of the invention can be affixed to an electrically conductive base. In a function-separated photoconductive element of the invention, either a CGL or a CTL may be closer to or in contact with the conducting base. In some cases, it may be desirable to use one or more intermediate subbing layers or additional CTLs between the conductive base and the CTL or CGL, or between the CTL and CGL to improve adhesion between the CTL, the CGLs and the conductive base and/or to act as an electrical barrier layer between the element and the conductive base.

Electrically conductive bases include, for example, paper (equilibrated to a relative humidity above 50 percent); aluminum-paper laminates; metal foils such as aluminum, zinc, etc.; metal plates, such as aluminum, copper, zinc, brass and galvanized plates; vapor deposited metal layers such as silver, chromium, nickel, aluminum and the like coated on paper or conventional photographic film supports, such as cellulose acetate, polystyrene, poly(ethylene terphthalate), etc. Such conductive materials as chromium, aluminum, or nickel can be vacuum deposited on transparent film supports in sufficiently thin layers to allow photoconductive elements prepared therewith to be exposed from either side of such elements. The support can be fabricated in any suitable configuration, for example, as a sheet, a drum, or an endless belt.

Electrical barrier layers, also known as charge-injection blocking layers, are used to prevent injection of charge carriers from the conducting layer or conductive support into the layer carrying the charge generation function. When such injection occurs, surface charges on the photoconductive element are dissipated in unexposed areas of its surface. Barrier layers are well known in the art and are typically composed of thin polymeric layers. Useful barrier layer materials include polyamides and the aforementioned polyester ionomers. Diamond-like carbon barrier layers useful in the photoconductive elements of the invention are disclosed in co-pending U.S. patent application Ser. No. 09/070,430 to Visser, Rimai, and Borsenberger, "Electrophotographic Elements Having DLC Charge-Injection Blocking Layers."

The barrier layer is coated directly on the electrically conductive base. Anodized aluminum substrates can serve as combined conductive base and barrier layer.

From the viewpoint of preparing photoconductive elements with long process lifetimes and resistance to wear, it is frequently desirable to prepare elements of the function-separated type in which the CTL is present as the outermost layer. The photoconductive elements of this invention, both single layer and function-separated, can also have protective layers as their outermost layers. When a protective layer is used, it may be in contact with or closest to either a CGL or a CTL. The use of protective layers to enhance the lifetime of photoconductive elements is well known to those skilled in the art. Examples of useful protective layers include sol-gels, diamond-like carbon, fluorinated diamond-like carbon, and silicon carbide. In order to prevent interference with the functions of the active layers, it is desirable to make the protective layers as thin as possible. However, thicker layers are frequently better able to provide the protective function. Thus, the thickness of the protective layers is a balance between these two requirements and can be suitably adjusted depending on the requirements of the user. In general, the thickness of the protective layer will vary between 0.05 and 5 $\mu$m. It is preferred that the thickness be between 0.05 and 1 $\mu$m. The protective layer can have a graduated composition or be composed of more than one layer in order to improve its protective ability or to achieve other goals, such as improved adhesion to underlying layers.

Photoconductive elements of the invention can include various additional layers known to be useful in electrophotographic elements, for example, subbing layers, overcoat layers, and screening layers.

Photoconductive elements of this invention can be used in electrophotographic processes in which only one polarity of charging is used. Such processes are well known to those skilled in the art. The photoconductive elements of the invention are of particular relevance for electrophotographic processes that use both polarities of charging. Such a process could use toners of two different polarities to form images of two colors or with two different surface textures, for example. The photoconductive elements of this invention could also advantageously be used, for example, in an electrophotographic process or apparatus that uses both charged area development (CAD) and discharged area development (DAD) with a single toner.

The following examples are presented for a further understanding of the invention.

EXAMPLE 1

BIND was synthesized as follows. An equimolar mixture of 1,4,5,8-naphthalenetetracarboxylic dianhydride and 4-amino-4',4"-dimethyl-triphenylamine in 4 picoline was refluxed for 2 hours, cooled in ice, and filtered. The solid was reslurried in dilute HCl, filtered, and rinsed with water. Column chromatography (silica gel eluted with toluene) and recrystallization from toluene yielded 58% of BIND, a pale purple solid with melting point 360° C.

The following analytical data confirm that the structure of the synthesized BIND is represented by the structure I. Proton NMR at 300 MHz gave the following lines for BIND in $CDCl_3$: d 8.83 (s, 4H, aromatic) 7.12 (s,24H, aromatic) 2.33 (s, 12H, methyl). Infrared analysis of BIND on a KBr plate gave peaks at 1717, 1679, 1600, 1585, 1506, 1447, 1345, 1320, 1293, 1278, and 1247 $cm^{-1}$. Calculated elemental compositions for BIND $C_{50}H_{40}N_4O_4$ are: 80.18% C, 4.98% H, 6.93% N. Elemental compositions found in synthesized BIND were: 79.63% C, 4.98% H, 6.84% N.

A bipolar photoconductive element was prepared as follows. A nickel-coated poly(ethylene terephthalate) (PET) conductive base was coated with a barrier layer solution made of a polyamide (sold under the tradename Amilon™ CM8000 by Toray Chemical Company) in an ethanol/1,1,2-trichloroethane 60:40 mixture. The solvent was removed, and the barrier layer dry thickness was about 0.5 μm. Onto the barrier layer, a 3000 Å thick CGL composed of the perylene CGM N,N-bis(2-phenethyl)-perylene-3,4,9,10-bis (dicarboximide)of structure IV was deposited by vacuum evaporation:

of 350 V in the dark, then exposing the element to 680 nm radiation, and measuring the change in voltage as a function of time. The exposure energy ($erg/cm^2$) is defined as the energy required to discharge the element from 350 V to 175 V (–350 V to –175 V if the initial charging polarity is negative) and is denoted as $E_{50\%}$; it is inversely related to the sensitivity. The exposure energy of the element after positive charging is denoted $E^+_{50\%}$. The exposure energy of the element after polarity charging is denoted $E^-_{50\%}$. The ability of the element to behave as a bipolar photoconductive element is measured by α, the ratio of the exposure energy under positive charging to that under negative charging: $α=E^+_{50\%}/E^-_{50\%}$. Values of α between 0.25 and 4.0 indicate that the element is a bipolar photoconductive element. The residual voltage is the fmal voltage on the photoconductive element and is denoted as $V_r$. Lower exposure energies and residual voltages are more desirable. The testing was performed using positive and negative initial charging. The results are shown in Table 1.

EXAMPLE 2

A bipolar photoconductive element was prepared as described in Example 1 except that the CGM used was of structure V:

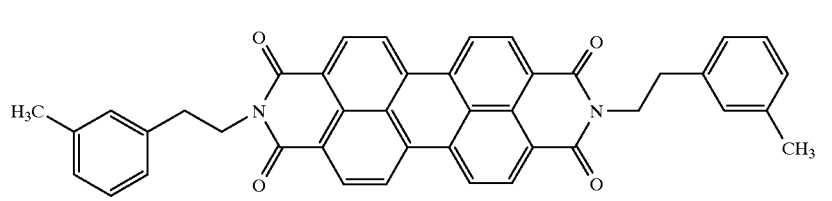

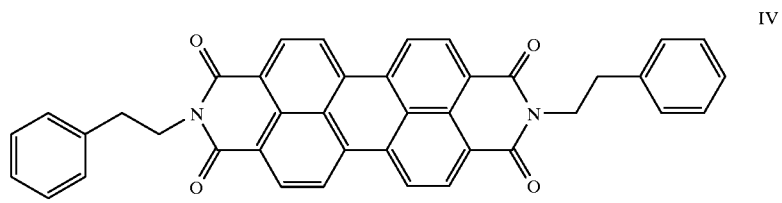

A CTL was prepared by mixing 30 weight percent BIND and 70 weight percent of the bisphenol-A polycarbonate Makrolon™ 5705 (Mobay Chemical Company) in dichloromethane to give a 10% solids solution. After the solids had dissolved, the solution was coated onto the CGL, and the solvent was allowed to evaporate to give a CTL with a dry thickness of 4.1 μm.

The sensitivity and residual voltage were measured by initially charging the photoconductive element to a potential and Lexan™ 145 (General Electric Company) was used as the binder in the CTL. The testing was completed as described in Example 1 and gave the results shown in Table 1.

EXAMPLE 3

A bipolar photoconductive element was prepared as described in Example 1 except that the CGM used was of structure VI:

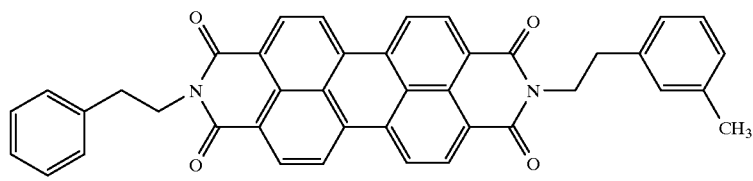

VI and Lexan™ 145 (General Electric Company) was used as the binder in the CTL. The testing was completed as described in Example 1 except that the initial charging was approximately 300 V. The testing gave the results shown in Table 1.

EXAMPLE 4

A bipolar photoconductive element was prepared as described in Example 1 except that the CGM used was of structure VII:

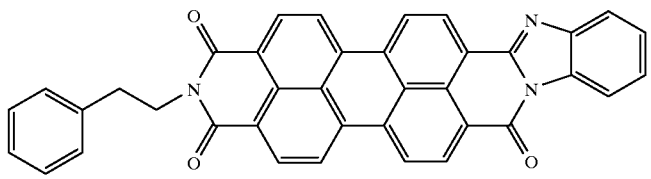

VII and Lexan™ 145 (General Electric Company) was used as the binder in the CTL. The testing was completed as described in Example 1 and gave the results shown in Table 1.

EXAMPLE 5

A bipolar photoconductive element was prepared as described in Example 1 except that the CGM used was of structure VIII:

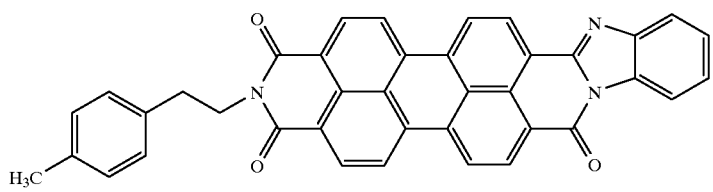

VIII and Lexan™ 145 (General Electric Company) was used as the binder in the CTL. The testing was completed as described in Example 1 except that the initial charging was approximately 250 V. The testing gave the results shown in Table 1.

COMPARATIVE EXAMPLE 1

A bipolar photoconductive element was prepared as described in Example 1 except that the CGM used was of structure IX:

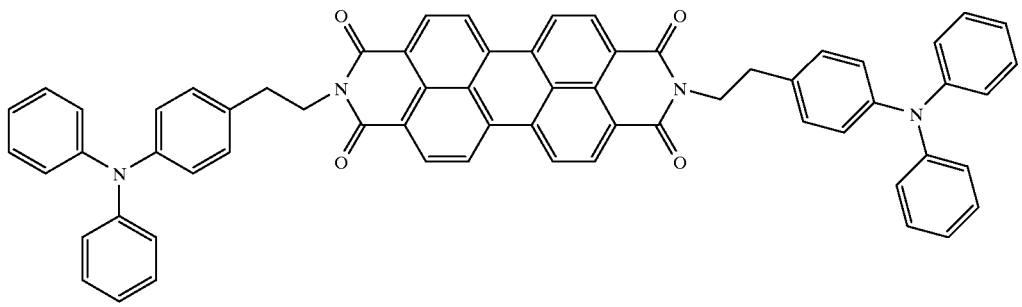

IX and Lexan™ 145 (General Electric Company) was used as the binder in the CTL. The testing was completed as described in Example 1 and gave the results shown in Table 1.

COMPARATIVE EXAMPLE 2

A bipolar photoconductive element was prepared as described in Example 1 except that the CGM used was of structure X:

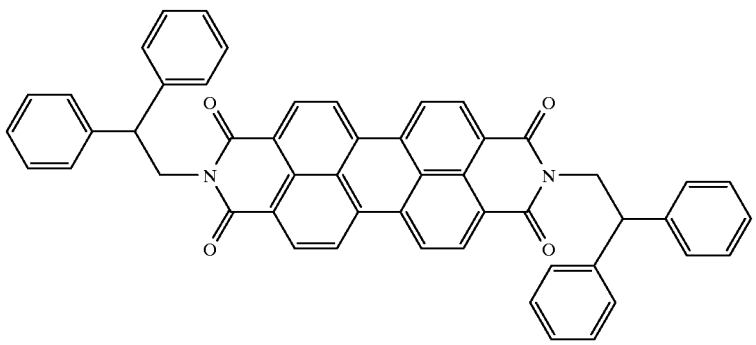

X and Lexan™ 145 (General Electric Company) was used as the binder in the CTL. The testing was completed as described in Example 1 and gave the results shown in Table 1.

COMPARATIVE EXAMPLE 3

A bipolar photoconductive element was prepared as described in Example 1 except that the CGM used was of structure XI:

and Lexan™ 145 (General Electric Company) was used as the binder in the CTL. The testing was completed as described in Example 1 and gave the results shown in Table 1.

COMPARATIVE EXAMPLE 4

A bipolar photoconductive element was prepared as described in Example 1 except that the CGM used was of structure XII:

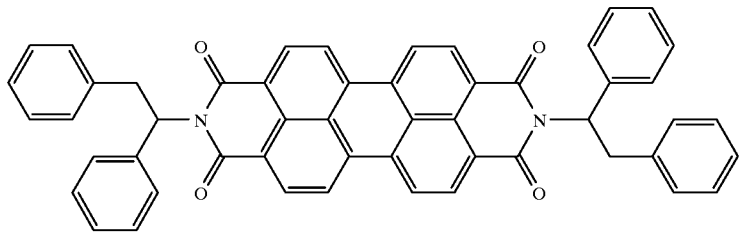

XI

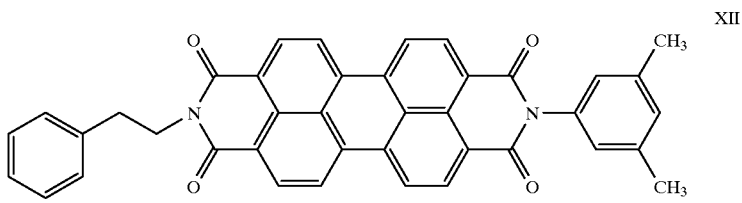

XII and Lexan™ 145 (General Electric Company) was used as the binder in the CTL. The testing was completed as described in Example 1 and gave the results shown in Table 1.

COMPARATIVE EXAMPLE 5

A bipolar photoconductive element was prepared as described in Example 1 except that the CGM used was of structure XIII:

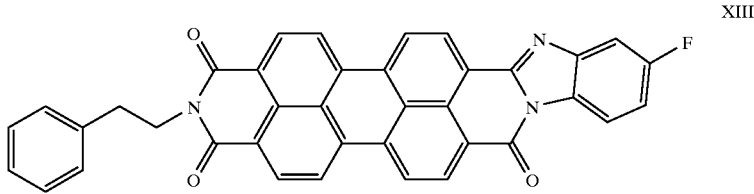

XIII and Lexan™ 145 (General Electric Company) was used as the binder in the CTL. The testing was completed as described in Example 1 and gave the results shown in Table 1.

COMPARATIVE EXAMPLE 6

A bipolar photoconductive element was prepared as described in Example 1 except that the CGM used was of structure XIV:

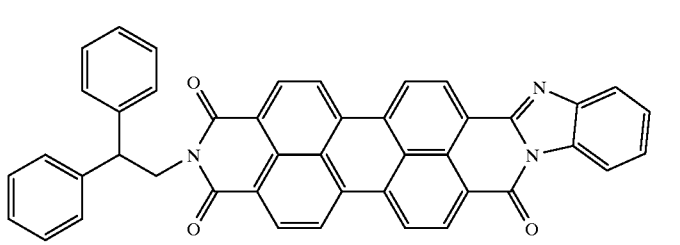

XIV and Lexan™ 145 (General Electric Company) was used as the binder in the CTL. The testing was completed as described in Example 1 and gave the results shown in Table 1.

COMPARATIVE EXAMPLE 7

A bipolar photoconductive element was prepared as described in Example 1 except that the CGM used was of structure XV:

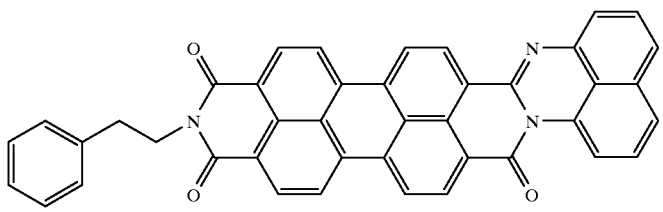

XV and Lexan™ 145 (General Electric Company) was used as the binder in the CTL. The testing was completed as described in Example 1 and gave the results shown in Table 1.

COMPARATIVE EXAMPLE 8

The photoconductive element of this example was prepared using cocrystalline mixtures of an unsubstituted titanyl phthalocyanine (TPC) and a titanyl tetrafluorophthalocyanine (TTFPC) as the CGM. The mixture was prepared as follows.

Preparation 1: Unsubstituted Titanyl Phthalocyanine

Phthalonitrile (1100 grams) and titanium tetrachloride (813 grams) were suspended in 6800 milliliters (ml) of 1-chloronaphthalene and heated to 215–220° C. and maintained for 2.5 hours at this temperature. The reaction mixture was cooled to 140° C., and the dark solid was collected and washed with acetone and methanol. After drying, the dark blue solid (1090 grams) was slurried twice in refluxing 10 liters of distilled water for two hours, filtered hot each time, and washed with acetone to yield crude phthalocyanine. The X-ray diffraction spectrum exhibits major peaks of the Bragg angle at 7.5, 8.3, 10.5, 12.7, 14.2, 14.6, 18.9, 22.1, 24.3, 26.1, and 29.9 (all ±0.2 degrees).

Preparation 2: Crude Titanyl Tetrafluorophthalocyanine

Tetrafluorophthalonitrile (38.7 grams, 0.267 mole) and titanium tetrachloride (20.7 grams, 0.134 mole) were suspended in 200 ml of 1-chloronaphthalene and heated to 210–215° C. and maintained for 2.5 hours at this temperature. The reaction mixture was cooled slightly, and the dark solid was collected and washed with acetone and methanol. After drying, the dark blue solid (34 grams) was slurried twice in refluxing dimethylformamide, filtered hot each time, and washed with acetone to yield crude titanyl tetrafluorophthalocyanine. The X-ray diffraction spectrum exhibits major peaks of the Bragg angle at 7.3, 10.6, 11.5, 11.8, 15.7, 16.6, 17.0, 18.2, 22.1, 23.2, 24.3, 27.0, and 31.2 (all ±0.2 degrees).

Preparation 3: Cocrystalline Mixture of Unsubstituted Titanyl Phthalocyanine and Titanyl Tetrafluorophthalocyanine 75:25

7.5 grams (g) of crude titanyl phthalocyanine and 2.5 g of crude titanyl tetrafluorophthalocyanine were mixed in a 16 ounce bottle with 300 g of 3 millimeter (mm) steel beads. The pigment sample was thus milled using a Sweco Vibro Energy grinding mill manufactured by Sweco, Inc., of Florence, Ky., for three days. The pigment particles completely fused, coating the stainless steel beads.

200 g of dichloromethane were added to the bottle. The mixture was further milled for 48 hours. Then the beads were separated, and the pigment was filtered, washed with dichloromethane, and dried. The X-ray diffraction spectrum of the dry-milled material exhibits three major broad peaks of the Bragg angle at 7.2, 15.4, and 25.5 (all ±0.2 degrees), depicting a very noncrystalline mixture. After the dichloromethane treatment, the X-ray diffraction spectrum of the material exhibits major peaks of the Bragg angle at 7.5, 10.2, 12.7, 13.2, 15.1, 16.1, 17.2, 18.5, 22.4, 24.2, 25.3, and 28.7 (all ±0.2 degrees).

The 75:25 cocrystalline mixture of unsubstituted titanyl phthalocyanine and titanyl tetrafluorophthalocyanine used to make the CGM of the photoconductive element of this Example was prepared as follows. A 2.5 gallon attritor (1S series), made by Union Process Company, was loaded at 53% with stainless steel 3 mm spheres media, 192 g of the cocrystal preparation 3, 48 g of poly[4,4-xylylene-co-2,2'-oxydiethylene) (46/54) isophthalate-co-5-sodiosulfoisophthalate 95/5], 1800 g of dichloromethane, and 1200 g of 1,1,2-trichloroethane. The media height was leveled with the liquid. The mixture was milled at 125 rpm for 3 hours. Then the mill was lowered to 100 rpm. A premixed solution consisting of 144 g of poly[4,4-xylylene-co-2,2'-oxydiethylene) (46/54) isophthalate-co-5-sodiosulfoisophthalate 95/5], 11369 g of dichloromethane, and 3444 g of 1,1,2-trichloroethane was added to the attritor. The mixture was milled at 100 rpm for 15 minutes. Then a mixture of 259.28 g of dichloromethane and 111.12 g of 1,1,2-trichloroethane was added. Mixing was continued for another five minutes before the dispersion was discharged through a screen and diluted to 2% solids.

A nickel-coated PET conductive base was coated with a barrier layer solution made of Amilon™ CM8000 in an ethanol/1,1,2-tiichloroethane 60:40 mixture. The solvent was removed, and the barrier layer dry thickness was about 0.5 μm. The dispersion was coated onto the barrier layer and the solvents removed to give a CGL with a dry thickness of 0.625 μm.

A CTL was prepared by mixing 30 weight percent BIND and 70 weight percent of the bisphenol-A polycarbonate Lexan™ 145 in dichloromethane to give a 10% solids solution. After the solids had dissolved, the solution was coated onto the CGL, and the solvent was caused to evaporate to give a CTL with a dry thickness of 4.1 μm.

Sensitometry testing was completed as described in Example 1 and gave the results shown in Table 1.

TABLE 1

| | | $E_{50\%}$ (erg/cm$^2$) | | | Residual voltage (V) | |
|---|---|---|---|---|---|---|
| Example or Comparative Example | CGM | When initial surface charge polarity is positive ($E_{50\%}^+$) | When initial surface charge polarity is negative ($E_{50\%}^-$) | α | When initial surface charge polarity is positive | When initial surface charge polarity is negative |
| Example 1 | perylene, structure IV | 12.5 | 7.2 | 1.73 | 75 | 20 |
| Example 2 | perylene, structure V | 41.7 | 35.7 | 1.17 | 125 | 62 |
| Example 3 | perylene, structure VI | 10.5 | 7.5 | 1.40 | 43 | 12 |
| Example 4 | perylene, structure VII | 19.5 | 8.7 | 2.24 | 120 | 17 |
| Example 5 | perylene, structure VIII | 9.6 | 9.9 | 0.97 | 103 | 12 |
| Comp. Ex. 1 | perylene, structure IX | no photo-induced discharge observed | | | | |
| Comp. Ex. 2 | perylene, structure X | no photo-induced discharge observed | | | | |
| Comp. Ex. 3 | perylene, structure XI | no photo-induced discharge observed | | | | |
| Comp. Ex. 4 | perylene, structure XII | no photo-induced discharge observed | | | | |
| Comp. Ex. 5 | perylene, structure XIII | no photo-induced discharge observed | | | | |
| Comp. Ex. 6 | perylene, structure XIV | no photo-induced discharge observed | | | | |
| Comp. Ex. 7 | perylene, structure XV | no photo-induced discharge observed | | | | |
| Comp. Ex. 8 | TPC/TTFPC | 19.2 | 2.1 | 9.14 | 107 | 5 |

TPC/TTFPC = unsubstituted titanyl phthalocyanine (TPC) and a titanyl tetrafluorophthalocyanine (TTFPC)

Discussion of Results

A bipolar charge transport material of structure I (BIND) was synthesized. The data of Examples 1–5 demonstrate that this molecule functions as a bipolar charge transport material that is useful in electrophotography.

In contrast to bipolar charge transport complexes that are known in the art, BIND offers the advantages of greater dispersibility at higher concentrations in binders, lower complexity of manufacture of photoconductive elements, and no known health risks associated with its use. Further, BIND is useful in producing bipolar photoconductive elements with higher sensitivity per unit thickness of the CTL than previously known molecular bipolar charge transport materials, such as TAND.

The combinations of perylene CGMs represented generally by structures II and III with BIND are shown by the senitometry data of Examples 1–5 to produce useful photoconductive elements. The elements have sensitivities that are similar under both positive and negative charging and have residual voltages that are acceptable for use in an electrophotographic apparatus.

The invention has been described in detail with particular reference to certain preferred embodiments thereof, but it will be understood that variations and modifications can be effected within the spirit and scope of the invention.

What is claimed:

1. A bipolar charge transport material that is useful in electrophotography, said bipolar charge transport material N,N'-bis-[p-(di-p-tolylamino)phenyl]-1,4,5,8-naphthalenetetracarboxylic acid having the structure:

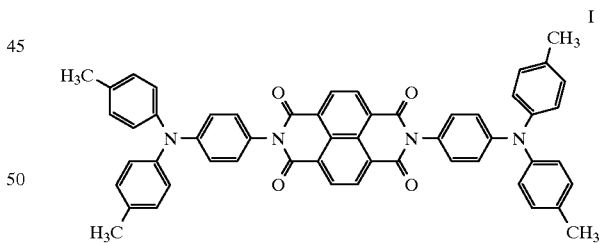

2. A photoconductive element comprising an electrically conductive base and at least one active layer, said active layer comprising N,N'-bis-[p-(di-p-tolylamino)phenyl]-1,4,5,8-naphthalenetetracarboxylic acid and at least one perylene charge generation material selected from the group consisting of the structures II and III:

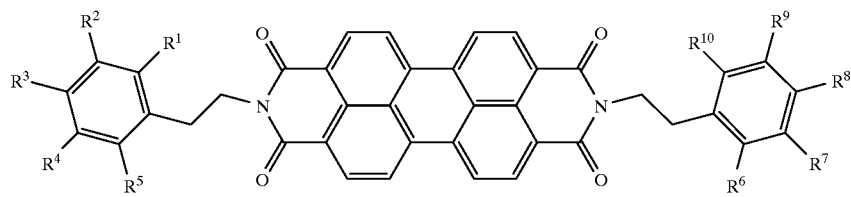

wherein $R^1, R^2, R^3, R^4, R^5, R^6, R^7, R^8, R^9$, and $R^{10}$ are, each independently, H, $CH_3$, or $C_2$–$C_4$ alkyl, linear or branched.

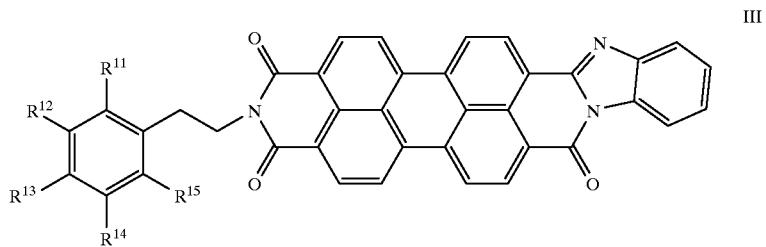

wherein $R^{11}$, $R^{12}$, $R^{13}$, $R^{14}$, and $R^{15}$ being, each independently, H, $CH_3$, or $C_2$–$C_4$ alkyl, linear or branched.

3. The photo conductive element of claim 2 wherein at least two of $R^1, R^2, R^3, R^4$, and $R^5$ are H and that at least two of $R^6, R^7, R^8, R^9$, and $R^{10}$ are H.

4. The photoconductive element of claim 2 wherein at least three of $R^1, R^2, R^3, R^4$, and $R^5$ are H and at least three of $R^6, R^7, R^8, R^9$, and $R^{10}$ are H.

5. The photoconductive element of claim 2 wherein all of $R^1, R^2, R^3, R^4, R^5, R^6, R^8, R^9$, and $R^{10}$ are H, and $R^7$ is $CH_3$.

6. The photoconductive element of claim 2 wherein all of $R^1, R^3, R^4, R^5, R^6, R^8, R^9$, and $R^{10}$ are H, and both $R^2$ and $R^7$ are $CH_3$.

7. The photoconductive element of claim 2 wherein all of $R^1, R^2, R^3, R^4, R^5, R^6, R^7, R^8, R^9$, and $R^{10}$ are H.

8. A photoconductive element according to claim 2 wherein $R^{11}$, $R^{13}$, $R^{14}$, and $R^{15}$ are H and $R^{12}$ is H.

9. A photoconductive element according to claim 2 wherein $R^{11}$, $R^{13}$, $R^{14}$, and $R^{15}$ are H and $R^{12}$ is $CH_3$.

10. The photoconductive element of claim 2 wherein the element additionally comprises a charge injection blocking layer between the active layer and the electrically conductive base.

11. The photoconductive element of claim 2 wherein the active layer is a single layer.

12. The photoconductive element of claim 2 wherein the active layer consists of at least one charge generation layer and at least one charge transport layer.

13. The photoconductive element of claim 2 wherein a protective layer is present as the outermost layer on the element.

14. The photoconductive element of claim 13 wherein the protective layer is comprised of diamond-like carbon.

15. The photoconductive element of claim 2 wherein the active layer consists of one charge generation layer and one charge transport layer.

* * * * *